US006225048B1

United States Patent
Soderberg-Naucler et al.

(10) Patent No.: US 6,225,048 B1
(45) Date of Patent: May 1, 2001

(54) DENDRITIC-MARKER EXPRESSING MACROPHAGE CULTURES AND METHODS OF REACTIVATING LATENT VIRUS

(75) Inventors: Cecilia E. Soderberg-Naucler, Hagarsten (SE); Kenneth N. Fish, San Diego, CA (US); Ashlee Moses, Portland, OR (US); Daniel Streblow, Tigard, OR (US); Jay Nelson, Tualatin, OR (US)

(73) Assignee: Oregon Health Sciences University, Portland, OR (US)

( * ) Notice: Subject to any disclaimer, the term of this patent is extended or adjusted under 35 U.S.C. 154(b) by 0 days.

(21) Appl. No.: 09/164,221

(22) Filed: Sep. 30, 1998

Related U.S. Application Data

(60) Provisional application No. 60/060,583, filed on Oct. 1, 1997.

(51) Int. Cl.[7] .............................. C12Q 1/70; G01N 33/53; C12N 5/00
(52) U.S. Cl. .............................. 435/5; 435/724; 435/325; 435/373
(58) Field of Search ............................... 435/5, 7.24, 325, 435/373

(56) References Cited

PUBLICATIONS

Perno et al., Inhibitio of Human Immunodeficiency Virus (HIV–1/HTLV–IIIBa–L) Replication in Fresh and Cultured Human Peripheral Blood Monocytes/Macrophages by Azidothymidine and Related 2',3"–Dideoxynucleosides, *The Journal of Experimental Medicine* 168:1111–1125, Sep. 1983.

Rusconi et al., Inhibition of Human Immunodeficiency Virus Type 1 Repuplication in Cytokine–Stimulated Monocytes/Macrophages by Combination Therapy, *The Journal of Infectious Diseases* 170: 1361–1366, 1994.

Weichold et al. Antisense Phosphorothioate Oligodeoxynucleotides Alter HIV Type 1 Replication in Cultured Human Macrophages and Peripheral Blood Monuclear Cell, *Aids Research and Human Retroviruses*, 11:(7) 863–867, 1995.

Lotze, Michael T. (1997) Getting to the Source: Dendritic Cells as Therapeutic Reagents for the Treatment of Patients With Cancer, *Annals of Surgery*, 266(1):1–5.

Rettig, M.B., et al. (1997) "Kaposi's Sarcoma–Associated Herpesvirus Infection of Bone Marrow Dendritic Cells from Multiple Myeloma Patients", *Science*, 276:1851–1854.

Caux, Christopher, et al. (1996) CD34[30] Hematopoietic Progenitors from Human Cord Blood Differentiate Along Two Independent Dendritic Cell Pathways in Response to GM–CSF + TNFα, *J. Exp. Med.*, 184:695–706.

Sallusto, Federica, et al. (1994) Efficient Presentation of Soluble Antigen by Culured Human Dendritic Cells IsMaintained by Granulocyte/Macrophage Colong–stimulating Factor Plus Interleukin 4 and Downregulated by Tumor Necrosis Factor α, *J. Exp. Med.*, 179:1109–1118.

Fish, Kenneth N., et al. (1996) "A Novel Mechanism for Persistence of Human Cytomegalovirus in Macrophages", *Journal of Virology*, 70(3):1855–1862.

Rice, G.P.A., et al. (1984) "Cytomegalovirus infects human lymphocytes and monocytes: Virus expression is restricted to immediate–early gene products". *Proc. Natl. Acad. Sci. USA*, 81:613406138.

Schrier, Rachel D., et al. (1990) "T–Cell Induced Expression of Human Imunodeficiency Virus in Macrophages", *Journal of Virology*, 64(7):3280–3288.

Matloubian, Mehrdad, et al. (1993) "Molecular Determinants of Macrophage Tropism and Viral Persistence: Importance of Single Amino Acid Changes in the Polymerase and Glycoprotein of Lymphocytic Choriomeningitis Virus", *Journal of Virology*, 67(12):7340–7349.

Gendelman, Howard E., et al. (1988) "Efficient Isolation and Propagation of Human Immunodeficiency Virus on Recombinant Colony–Stimulating Factor 1–Treated Monocytes", *J. Exp. Med.*, 167:1428–1441.

Sinzger, Christian, et al. (1996) "Tissue Macrophages Are Infected by Human Cytomegalovirus In Vivo", *The Journal of Infectious Diseases*, 173:240–245.

Ibanez, Carlos E., et al. (1991) "Human Cytomegalovirus Productively Infects Primary Differentiated Macrophages", *Journal of Virology*, 65(12):6581–6588.

Wiederman, Jean–Taylor, et al. (1991) "Monocytes are a major site of persistence of human cytomegalovirus in peripheral blood mononuclear cells", *Journal of General Virology*, 72:2059–2064.

Meyers, Joel, D. (1986) "Infection in Bone Marrow Transplant Recipients", *The American Journal of Medicine*, 81(1A):27–38.

Chou, Sunwen (1986) "Acquisition of Donor Strains of Cytomegalovirus by Renal–Transplant Recipients", *The New England Journal of Medicine*, 314(22):1418–1423.

Schmader, Kenneth E. (1992) "Aging and Reactivation of Latent Murine Cytomegalovirus", *The Journal of Infectious Diseases*, 166:1403–1407.

Soederberg–Naucler, C., et al. (1977) "Reactivation of Latent Human Cytomegalovirus by Allogeneic Stimulation of Blood Cells from Healthy Donors" *Cell*, 91:119–126.

Soederberg–Naucler, C., et al. (1997) "Reactivation of infectious human cytomegalovirus from allogeneically stimulated T–cell induced monocyte derived macrophages from asymptomatic seropositive individuals" 6th International Cytomegalovirus Workshop, Mar. 5–9, 1997, Abstract: A–21, No. 41.

Soederberg–Naucler, C., et al. (1997) "Reactivation of Human Cytomegalovirus in a Novel Dendritic Cell Type in Healthy Blood Donors", *International Herpevirus Workshop*, Aug. 5, 1997, Abstract No. 327.

*Primary Examiner*—Hankyel T. Park
(74) *Attorney, Agent, or Firm*—Townsend and Townsend and Crew LLP

(57) ABSTRACT

The present invention provides methods of latent virus reactivation in monocyte-derived macrophages through allogeneic stimulation of peripheral blood mononuclear cells ("PBMC"), methods of culturing virus, and cultures of virally permissive monocyte-derived macrophages.

80 Claims, No Drawings

DENDRITIC-MARKER EXPRESSING MACROPHAGE CULTURES AND METHODS OF REACTIVATING LATENT VIRUS

CROSS REFERENCE TO RELATED APPLICATIONS

This application claims the benefit of U.S. Pat. Ser. No. 60/060,583, filed Oct. 1, 1997, herein incorporated by reference in its entirety.

FEDERALLY SPONSORED RESEARCH OF DEVELOPMENT

This invention was made with Government support under Grant No. AI 21640, awardedby the National Institutes of Health. The Government has certain rights in this invention.

FIELD OF THE INVENTION

The present invention provides methods of culturing virus in monocyte-derived macrophages ("MDM") through allogeneic stimulation of peripheral blood mononuclear cells ("PBMC") or through culture of PBMC with media comprising IFNγ, stable cultures of such virally permissive monocyte-derived macrophages, and methods of screening for viral inhibitors using such cultures.

BACKGROUND OF THE INVENTION

Human cytomegalovirus ("HCMV") is a ubiquitous pathogen that is the major cause of morbidity and mortality in immunocompromised individuals, such as transplant and AIDS patients, as well as a leading cause of congenital birth defects (Britt et al., in Fields Virology, pp. 2493–2523 (Fields et al., eds. 1996)). HCMV is also associated with the development of atherosclerosis, restenosis after coronary angioplasty, chronic rejection in organ transplant patients (Grattan et al., Jama 261:3561–3566 (1989); Melnick et al., Bioessays 17:899–903 (1995); Zhou et al., NEJM 335:624–630 (1996)) and chronic graft-versus-host disease in bone marrow transplant patients (Lönnqvist et al., Transplantation 38:465–468 (1984); Söderberg et al., Transplantation 61:600–609 (1996)). Most individuals become infected with HCMV early in life, and depending on the geographic location, between 60–100% of adults are carriers of the virus (Britt et al., in Fields Virology pp. 2493–2523 (Fields et al., eds. 1996)).

Similar to other herpesviruses, HCMV establishes lifelong latency in the host after a primary infection, which is characterized by persistence of the viral genome without the production of infectious virus. The respective sites of latency for other herpesviruses such as Epstein Barr and herpes simplex viruses are B cells and neurons (Kieff, in Fields Virology pp. 2343–2396 (Fields et al., eds. 1996); Roizman et al., in Fields Virology pp. 2231–2296 (Fields et al., eds. 1996)). However, although transmission of latent HCMV has been shown to occur through transfusion of blood products, bone marrow grafts, and solid organs (Britt et al., in Fields Virology pp. 2493–2523 (Fields et al., eds. 1996); Chou, NEJM 314:1418–1423 (1986); Meyers, Am. J. Med. 81:27–38 (1986); Tegtmeier, Arch. Pathol. Lab. Med. 113:236–245 (1989)), the identity of cells harboring latent or persistent virus is unknown. In addition to HCMV, the identity of cells harboring other viruses is unclear, and methods of culturing such viruses are unknown.

Several animal models have been established to understand mechanisms involved in latency and reactivation of CMV (Bruning et al., Transplantation 41:695–698 (1986); Hamilton et al., Transplantation 39:290–296 (1985); Reddehase et al., J. Exp. Med. 179:185–193 (1994); Yagyu et al., Transpl. Proc. 25:1152–1154 (1993)). In murine organ transplant models, reactivation of murine cytomegalovirus ("MCMV") was shown to be influenced by the state of imrnmunosuppression and histoincompatibility between the donor and the recipient (Bruning et al., Transplantation 41:695–698 (1986); Hamilton et al., Transplantation 39:290–296 (1985); Reddehase et al., J. Exp. Med. 179:185–93 (1994); Yagyu et al., Transpl. Proc. 25:1152–1154 (1993)). In MCMV latently-infected mice, the spleen, kidneys, and bone marrow were shown to be important sources of virus (Jordan et al., J. Clin. Invest. 70:762–768 (1982); Mercer et al., J. Virol. 62:987–997 (1988); Olding et al., J. Exp. Med. 141:561–572 (1975)). Activation of virus in latently infected animals has been shown to occur through either intraperitoneal injection of thioglycollate (Pollock et al., Virology 227:168–179 (1997)) or allogeneic stimulation (Schmader et al., J. Inf. Dis. 166:1403–1407 (1992)). The peripheral blood of latently infected animals was also demonstrated to be a reservoir of virus since allogeneic stimulation resulted in the activation of MCMV replication (Schmader et al., J. Inf. Dis. 166:1403–1407 (1992); Olding et al., J. Exp. Med. 141:561–572 (1975); Jordan et al., J. Clin. Invest. 70:762–876 (1982); Mercer, et al., J. Virol. 62:987–997 (1988); Koffron et al., Scand. J. Inf. Dis.-Suppl. 99:612 (1995); Stoddart et al., J. Virol. 68:6243–6253 (1994); Pollock et al., Virology 227:168–179 (1997)).

In humans, examination of organ tissues and peripheral blood obtained from patients with HCMV disease has suggested that PBMC are a viral reservoir of HCMV (Chou, NEJM 314:1418–1423 (1986); Meyers, Am. J. Med. 81:27–38 (1986); Taylor-Wiedeman, et al., J. Gen. Virol. 72:2059–2064 (1991); Tegtmeier, Arch. Pathol. Lab. Med. 113:236–245 (1989); Gnann et al., Am. J. Pathol. 132:239–248 (1988)). Further analyses of separated PBMC populations obtained from HCMV-seropositive donors have identified monocytes as the predominant infected cell type (Taylor-Wiedeman et al., J. Gen. Virol. 72:2059–2064 (1991)). While viral replication in monocytes is restricted to early events of gene expression (Ibanez et al., J. Virol. 65:6581–6588 (1991)), examination of organ tissues early in HCMV disease has demonstrated extensive viral gene expression in tissue macrophages (Gnann et al., Am. J. Pathol. 132:239–248 (1988); Sinzger et al., J. Inf. Dis. 173:240–245 (1996)).

CD14$^+$ monocytes in the peripheral blood are terminally differentiated cells derived from myeloid/granulocyte precursors. In vivo, stimulation of monocytes by contact with T and B cells during antigen processing events induces differentiation of monocytes into macrophages for function as immune effector cells. A variety of tissue culture protocols have been established to mimic the in vivo development of monocyte-derived macrophages ("MDM"), which includes treatment of monocytes with cytokines, mitogens, corticosteroids, or lipopolysaccharide ("LPS") (reviewed by Adams et al., in The Macrophage pp. 77–115 (Lewis et al., eds. 1992)). Caux et al. report, using FACS sorting, that a transient population of CD14$^+$, CD1a$^+$ cells represent a developmental phase in MDM differentiation (Caux et al., J. Exp. Med. 184:695–706 (1996)). MDM derived by these methods have been used for the in vitro propagation of certain macrophage-tropic viruses (Gendelman et al. J. Exp. Med. 167:1428–1441 (1988); Matloubian et al., J. Virol. 67:7340–7349 (1993); Schrier et al., J. Virol. 64:3280–3288 (1990)). Rettig et al. identify endogenous CD68$^+$, CD83$^+$ bone marrow stromal cells that are infected with HHV8 (Rettig et al., *Science* 276:1851–1854 (1997)). However, culture of HCMV in MDM has proven to be difficult, often resulting in abortive infection (Rice et al., *Proc. Natl. Acad. Sci.* (*USA*) 81:6134–6138 (1984); Taylor-Wiedeman et al.,*J. Virol.* 68:1597–1604 (1994)).

MDM differentiation systems have also been developed that rely on the mitogenic stimulation of PBMC to generate HCMV permissive macrophages (Ibanez et al., *J. Virol.* 65:6581–6588 (1991)). Although macrophages differentiated by this method are susceptible to in vitro, exogenous HCMV infection, attempts to reactivate HCMV from PBMC obtained from latently infected individuals have been unsuccessful using this method or others (Taylor-Wiedeman et al., *J. Virol.* 68:1597–1604 (1994)). Thus, there is a need to identify the specific cellular reservoir of latent HCMV infection, to isolate cultures of such cells, and to establish methods of culturing cells in which HCMV replicates, where the cells are latently infected with HCMV and/or additional viruses, or can be infected in vitro.

SUMMARY OF THE INVENTION

The present invention identifies for the first time the specific cellular reservoir of latent viral, e.g., HCMV infection. The invention also provides methods of reactivating HCMV and other viruses in long-term cultures of allogeneically-stimulated monocyte-derived macrophages ("MDM"). Infectious virus was recovered from a myeloid lineage cell phenotype of MDMs that expressed both macrophage (CD14) and dendritic cell markers (CD83). In addition, these cells are permissive for exogenous viral infection. These observations provide the first evidence that HCMV and other viruses establish a true latent state in myeloid lineage cells in the peripheral blood, which reactivate upon allogeneic stimulation.

In one aspect, the invention provides a method of replicating viruses, including mammalian viruses, in virally permissive monocyte-derived macrophages. The method includes the steps of: (a) culturing monocytes under conditions where the monocytes are in fluid communication with viable, allogeneically stimulated peripheral blood mononuclear cells ("PBMC") to activate the monocytes to differentiate into monocyte-derived macrophages or culturing the monocytes under conditions where the monocytes are exposed to conditioned media comprising IFN-γ in an amount sufficient to activate the monocytes to differentiation into virally permissive monocyte-derived macrophages; and (b) permitting viral replication in the monocyte-derived macrophages, where the virus is either latent in the monocytes or exogenously added to the culture.

In another aspect, the invention provides a method for screening for inhibitors of virus production using virally permissive monocyte-derived macrophages. This method includes the steps of: (a) culturing monocytes under conditions where the monocytes are in fluid communication with viable, allogeneically stimulated peripheral blood mononuclear cells ("PBMC") to activate the monocytes to differentiate into monocyte-derived macrophages or culturing the monocytes under conditions where the monocytes are exposed to conditioned media comprising IFN-γ in an amount sufficient to activate the monocytes to differentiation into virally permissive monocyte-derived macrophages; (b) permitting viral replication in the monocyte-derived macrophages, where the virus is either latent in the monocytes or exogenously added to the culture; (c) contacting the monocyte-derived macrophages of step (b) with substances suspected of having the ability to inhibit viral production; and (d) detecting the level of virus production in the monocytes-derived macrophages.

In another aspect, the invention provides a culture of virally permissive monocyte-derived macrophages, where the monocyte-derived macrophages are derived from monocytes exposed to allogeneically stimulated peripheral blood mononuclear cells ("PBMC") or are exposed to conditioned media comprising IFN-γ in an amount or concentration sufficient to and for a time sufficient to: (i) stimulate active differentiation of the monocytes into virally permissive monocyte-derived macrophages, and (ii) stimulate viral production in the monocyte-derived macrophages; and, where the virally permissive monocyte-derived macrophages produce at least 10,000 fold greater virus than non-allogeneically stimulated monocytes.

In another aspect, the invention provides a culture of virally permissive monocyte-derived macrophages having a population further defined as at least 85% bearing CD83 and CD14. In another aspect, the invention provides a culture of virally permissive monocyte-derived macrophages having a population further defined as at least 85% bearing CD83, CD68, CD1a, CD64, and CD14.

In another aspect, the present invention provides a stable culture of virally permissive monocyte-derived macrophages having the following characteristics: (i) comprising dendritic cell markers CD68, CD83, and CD1a; (ii) comprising macrophage cell markers CD64 and CD14; and (iii) derived from CD14$^+$ monocytes.

In another aspect, the invention provides a method of culturing virally permissive monocyte-derived macrophages. This method includes the step of culturing monocytes under conditions where the monocytes are in fluid communication with viable, allogeneically stimulated peripheral blood mononuclear cells ("PBMC") or culturing the monocytes under conditions where they are exposed to media comprising IFN-γ, to activate the monocytes to differentiate into monocyte-derived macrophages.

In one embodiment, the monocyte derived-macrophages have a majority population of cells bearing CD83 and CD14. In another embodiment, the monocyte-derived macrophages have a majority population of cells bearing CD83, CD68, CD1a, CD64, and CD14. In another embodiment, monocyte-derived macrophages have a population of cells where 85% of the cells bear CD83, CD68, CD1a, CD64, and CD14. the In one embodiment, the monocyte-derived macrophages are human. In one embodiment, the allogeneically stimulated cells include CD4$^+$ and CD8$^+$ cells.

In one embodiment, the mammalian virus is selected from the group consisting of cytomegalovirus ("CMV"), hepatitis C virus ("HCV"), human immunodeficiency virus ("HIV"), human herpes virus 6 ("HHV6"), human herpes virus 7 ("HHV7"), and human herpes virus 8 ("HHV8"). In one embodiment, the virus is latent.

In one embodiment, the substances are inhibitors of viral proteases. In another embodiment, the substances are antisense molecules that bind to nucleic acid generated by the virus. In one embodiment, the substances are antisense molecules that are complementary to mRNA encoded by a viral genome. In one embodiment, the substances are ribozymes complementary to mRNA encoded by a viral genome. In one embodiment, the substances inhibit a viral protein selected from the group consisting of CMV DNA polymerase, UL80, and UL89.

BRIEF DESCRIPTION OF THE DRAWINGS

Not applicable.

DETAILED DESCRIPTION OF THE INVENTION

I. Introduction

The present invention describes for the first time monocyte-derived macrophages ("MDM") that express dendritic markers and that harbor latent viral, e.g., HCMV, infections. These cultures are virally permissive, that is, they support reactivation of latent infections and are also capable of being productively infected with exogenous virus. The invention thus provides virally permissive cultures of MDM, methods of culturing the virally permissive MDM, and methods of using the cultures to identify inhibitors of viral production.

Importantly, this invention describes an in vitro system that can be used to study viruses; for example, to identify mechanisms involved in the maintenance of viral latency and to explore the cellular activation pathways that mediate latent virus reactivation and initial virus infection. Furthermore, these cells and methods of culture provide an important tool to examine mechanisms of viral immunological surveillance. These cells and methods of culture are also useful for identifying therapeutic approaches to prevent viral reactivation and to inhibit viral production. The cells and methods of the invention are also useful for diagnosing patients that have latent virus infection, by providing a means of culturing latently infected cells and examining the cells for the presence of the viral genome.

II. Definitions

As used herein, the following terms have the meanings ascribed to them unless specified otherwise.

"Replicating" refers to the ability of a virus to duplicate and transcribe its genome, as a means to produce infectious particles from a cell.

"Virally permissive" refers to a characteristic of a cell, e.g., a monocyte-derived macrophage, where the cell is capable of being productively infected by an exogenous virus or of reactivating a latent viral infection, e.g., HHV6, HHV7, HHV8, CMV, HCV, and HIV.

"Stable culture" refers to a culture of terminally differentiated cells, as opposed to cells that appear transiently during development and then further differentiate.

"Allogeneic stimulation" refers to a cellular differentiation and/or proliferative event among immune cells (e.g., B cells, T cells, monocytes, and the like) that is either: (1) mediated by cells triggered to produce soluble factors such as cytokines by antigen contact or mixing of cells with different MHC haplotypes ("cell-mediated"); or (2) mediated directly by soluble factors, e.g., cytokines such as IFN-γ ("cytokine-mediated"). For example, during allogeneic stimulation, monocytes are activated to differentiate into monocyte-derived macrophages. Similarly, T cells are activated to proliferate and differentiate into cytotoxic or helper T cells and the like. Typically, the allogeneic stimulation event of the invention occurs in vitro. For cell-mediated allogeneic stimulation, typically a heterogenous population of cells such as PBMC are mixed with PBMC of a different haplotype. For direct cytokine-mediated allogeneic stimulation, PBMC or a more homogenous population of cells is used. the cytokinemediated stimulation can occur using conditioned medium (i.e., medium in which cells were grown) or in medium to which cytokines have been exogenously added.

"Fluid communication" refers to cells in communication in an aqueous solution. Fluid communication includes communication mediated by direct contact between cells in aqueous solution, or communication between cells that are separated by semipermeable membranes, where the communication is mediated by soluble factors, e.g., cytokines, in aqueous solution.

"Peripheral blood mononuclear cells" or "PBMC" refers to a heterogeneous population of hematolymphoid cells derived from blood, from which the red blood cells have been removed.

"Monocyte" refers to a differentiated cell of the mononuclear phagocyte lineage, e.g., those that are $CD14^+$ (see, e.g., *Fundamental Immunology* (Paul ed., 3d ed. 1993)).

"Monocyte-derived macrophage" or "MDM" is a type of antigen presenting cell of the mononuclear phagocyte lineage derived from monocytes that have further differentiated into macrophages (see, e.g., Paul, supra).

"Culturing" refers to growing cells ex vivo or in vitro.

"Latent" refers to a type of viral infection in which the host cells contain the genome of the virus, but where expression of the genome is wholly or partially repressed. A latent infection can be "reactivated" to produce viral replication, transcription, and production of infectious particles (see, e.g., White & Fenner, *Medical Virology* (4th ed., 1994)).

"CD83," "CD14," "CD68," "CD1a," "CD64," "CD4," and "CD8" are names of specific cell surface molecules. These cell surface molecules are often associated with specific cell types and can be used as markers to identify specific cells (see, e.g., Paul, supra). For example, CD4 and CD8 are T-cells markers, CD83, CD68, and CD1a are dendritic cell markers, and CD14, and CD64 are macrophage markers. The combination of CD14 and CD83 can be used to identify virally permissive monocyte-derived macrophages. CD68, CD1a, CD64, CD14, and CD83 can also be used in combination to identify virally permissive MDM (Allo-MDM).

"Ribozyme" refers to a catalytic RNA molecule that cleaves a target RNA having particular nucleic acid sequences through ribonuclease activity. General methods for the construction of ribozymes, including hairpin ribozymes, hammerhead ribozymes, RNase P ribozymes (i.e., ribozymes derived from the naturally occurring RNase P ribozyme from prokaryotes or eukaryotes) are known in the art (see, e.g., Castanotto et al., *Advances in Phannacology* 25:289–317 (1994) (providing an overview of ribozymes in general, including group I ribozymes, hammerhead ribozymes, hairpin ribozymes, RNase P, and axhead ribozymes)).

An "antisense" nucleic acid refers to a nucleic acid that is complementary to a target sequence of choice and capable of specifically hybridizing with the target molecules. The term antisense also encompasses a DNA sequence in an expression cassette from which antisense RNA is transcribed. Antisense nucleic acids hybridize to a target polynucleotide and interfere with the transcription, processing, translation or other activity of the target nucleic acid. An antisense nucleic acid can inhibit DNA replication or DNA transcription by, for example, interfering with the attachment of DNA or RNA polymerase to the promoter by binding to a transcriptional initiation site or a template. It can interfere with processing of mRNA, poly(A) addition to mRNA or translation of mRNA by, for example, binding to regions of the RNA transcript such as the ribosome binding site. It can promote inhibitory mechanisms of the cells, such as promoting RNA degradation via RNase action. The inhibitory polynucleotide can bind to the major groove of the duplex DNA to form a triple helical or "triplex" structure. Methods of inhibition using antisense nucleic acids therefore encompass a number of different approaches to altering expression of specific genes that operate by different mechanisms (see, e.g., Helene & Toulme, *Biochim. Biophys. Acta.,* 1049:99–125 (1990)).

A nucleic acid that is "complementary" to another refers to a nucleic acid capable of binding to a target nucleic acid through base pairing involving hydrogen bond formation. Complementary hybridization between a nucleic acid and a target sequence occurs when the nucleic acid binds substantially only to the target sequence, forming a hybridization complex, when the target is in a heterogeneous mixture of polynucleotides and other compounds. Such hybridization is determinative of the presence of the target sequence. Although the complementary nucleic acid may bind other unrelated sequences, at least 80%, preferably 90% or more of the hybridization complexes formed are with the target sequence.

"Viral production" and "produce a virus" refer to the ability of a cell infected with a virus to replicate and transcribe a viral genome and/or to make viral particles. The infection can be a reactivated latent infection, or infection via exogenously added virus. The virus can be either a wild-type or mutated virus. Viral mutations include both naturally occurring, chemically or physically induced or recombinantly introduced.

"Inhibition of viral production" and viral "inhibitors" refer to molecules that interfere with any step of the viral life cycle, e.g., reactivation of latent infection, initial infection, viral replication, viral transcription, viral translation, and packaging of viral particles. Such molecules can be identified using the cultures of the invention and can be molecules such as protein inhibitors, antisense nucleic acid, ribozymes, and the like. Monocyte-derived macrophages that are treated with a substance suspected of having the ability to inhibit viral production are compared to control samples without the inhibitor, to examine the extent of inhibition. Control samples (untreated with inhibitors) are assigned a relative viral production value of 100. Inhibition of viral production is achieved when the viral production value relative to the control is about 75, preferably 50, more preferably 25.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Cassol et al., 1992; Rossolini et al., *Mol. Cell. Probes* 8:91–98 (1994)). The term nucleic acid is used interchangeably with gene, cDNA, and MRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the complementary target nucleic acid sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)$'_2$ a dimer of Fab which itself is a light chain joined to $V_H$—$C_H1$ by a disulfide bond. The F(ab)$'_2$ may be reduced under mild conditions to break the disulfide linkage in the hinge region, thereby converting the F(ab)$'_2$ dimer into an Fab' monomer. The Fab' monomer is essentially an Fab with part of the hinge region (see *Fundamental Immunology* (Paul, ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

The term "immunoassay" is an assay that uses an antibody to specifically bind an analyte. The immunoassay is characterized by the use of specific binding properties of a particular antibody to isolate, target, and/or quantify the analyte.

III. Monocyte-derived Macrophages

Macrophages are terminally differentiated cells that originate from a precursor stem cell found in bone marrow. This stem cell is thought to be a common multipotential stem cell that eventually leads to all the cells of the hematolymphoid system (see, e.g., *Fundamental Immunology* (Paul ed., 3d ed. (1993); *Immunology* (Hood et al., eds., 2d ed. 1984)). Within particular maturational microenvironments, this multipotential stem cell develops into a myeloid stem cell, and then commits to a specific developmental lineage (see, e.g., Paul, supra, for a discussion of proteins involved in monocyte-derived macrophage differentiation).

Developmental commitment to the macrophage lineage is demonstrated by the monocyte, which is a differentiated precursor of a macrophage. Monocytes are found circulating in the blood, in tissues, and in a storage compartment presumably located in the bone marrow. In tissues, monocytes develop further into macrophages. Under normal circumstances, neither monocytes or macrophages divide.

Macrophages are found in all tissues, in surrounding blood vessels, and close to epithelial cells. Macrophages in different tissues can develop distinctive properties. For example, macrophages from peritoneal cavity, lung, liver, kidney, bone marrow, and spleen have different cell receptors, expression of MHC class II molecules, and oxidative metabolism. Their main function is to investigate the environment, respond to stimuli, and present antigen via MHC class II. Therefore, macrophages are active in pinocytosis, where they sample extracellular fluid, and they also express surface receptors to a wide range of molecules. In this manner, macrophages can take up microorganisms and respond to cytokines and foreign proteins. In response to these environmental stimuli, the macrophages present internalized antigen to other cells of the immune system, and they secrete a variety of molecules. Thus, macrophages participate in inflammation and immunological reactions, such as antigen presentation to T cells via MHC class II molecules.

IV. Cell Culture and Allogeneic Stimulation

A. Allogeneic Stimulation and Viral Infection or Reactivation

The monocyte-derived macrophage cultures of the invention are derived from an allogeneic stimulation reaction. The cells that are subjected to allogeneic stimulation are isolated from any suitable source and may be heterogenous or homogenous, e.g., peripheral blood mononuclear cells ("PBMC") or monocytes. For cell-mediated allogeneic stimulation reactions, PBMC are typically used as the source of the monocyte-derived macrophage cultures of the invention. PBMC contain approximately 4–6% monocytes. Monocytes can also be quickly isolated with a 2 hour adherence.

PBMC are prepared from whole blood samples by separating mononuclear cells from red blood cells. There are a number of methods for isolating PBMC, e.g., velocity sedimentation, isopyknic sedimentation, affinity purification, and flow cytometry. Typically, PBMC are separated from red blood cells by density gradient (isopyknic) centrifugation, in which the cells sediment to an equilibrium position in the solution equivalent to their own density. For density gradient centrifugation, physiological media should be used, the density of the solution should be high, and the media should exert little osmotic pressure. Density gradient centrifugation uses solutions such as sodium ditrizoate-polysucrose, Ficoll, dextran, and Percoll (see, e.g., Freshney, *Culture of Animal Cells* (3rd ed. 1994)). Such solutions are commercially available, e.g., HISTOPAQUE® (Sigma).

Typically, anticoagulated whole blood or plasma is layered onto the gradient and centrifuged according to standard procedures (see, e.g., Fish et al., *J. Virol.* 69:3737–3743 (1995)). Using, e.g., the procedure in Fish et al., the red blood cells and granulocytes form a pellet, while lymphocytes and other mononuclear cells such as monocytes remain at the plasma/density gradient interface (see, e.g., Freshney, *Culture of Animal Cells* (3rd ed. 1994)).

After the cells of choice are isolated, they are cultured under conditions that give rise to allogeneic stimulation and differentiation of monocytes into mono-cytederived macrophages ("MDM"). Cell-mediated allogeneic stimulation is a proliferative and differentiation response to mismatched haplotypes and antigen. Allogeneic stimulation via mixed haplotypes is commonly known as a mixed lymphocyte or leukocyte reaction ("MLR"). An example of a well-known MLR is a "one way" reaction, in which PBMC from two individuals are mixed, where the cells from one individual have been inactivated by irradiation or treatment with mitomycin C. Because one set of cells is inactivated, only the other set undergoes the proliferative response. However, in the cultures of the invention, the reaction can also be performed as a "two way" reaction, in which both cell sets are stimulated to proliferate. Thus, the MDM cultures of the invention may have one or more genotypes.

Because allogeneic stimulation depends on cytokine production by cells, MDM can also be cultured under conditions where monocytes are separated from allogeneically stimulated PBMC, using semipermeable membranes. Cells, typically PBMC, from donors with two different haplotypes are mixed and placed in one compartment, while cells, e.g., PBMC or a more homogenous monocyte population (from one of the two donors or a third donor) are placed in a second compartment. The two compartments are separated by semipermeable membranes, where the compartments are in fluid communication. In this manner, the soluble factors produced by the allogeneically stimulated PBMC in the first compartment are available to stimulate the monocytes in the second compartment to differentiate into MDM. One example of such a culture apparatus is a transwell system (commercially available), in which a small well with a 0.45 micron membrane at the bottom is placed inside a larger well. The monocytes or PBMC to be differentiated into MDM are placed in the small well, and the haplotype mixed PBMC are in the larger outside well. Conditioned medium or transwell systems can be used for cytokine-mediated allogeneic stimulation. Medium can also be used for cytokine-mediated stimulation into which the cytokines have been exogenously added, and the medium has not been previously contacted with cells.

Because cytokines promote differentiation of monocytes into mono-cytederived macrophages, allogeneic stimulation can also be performed in a cell-free system. In a cell free, cytokine-mediated allogeneic stimulation reaction, PBMC or monocytes from a single individual are directly treated with cytokines such as IFN-γ to activate differentiation of monocytes into MDM (see, e.g., Example II). This type of allogeneic stimulation reaction is referred to as cytokine-mediated allogeneic stimulation.

For example, in one type of cell-mediated allogeneic stimulation reaction using mixed haplotypes, typically equal numbers of viable cells from two different blood donors are mixed. The cells are plated at a concentration of about between $1\times10^6$ to $1\times10^8$ cells per ml, preferably approximately $1-2\times10^7$ cells per ml. Preferably, an adherence medium such as Iscove's complete medium is used for plating. The medium typically contains antibiotics, e.g., penicillin, streptomycin, kanamycin, gentamicin, mycostatin and the like, preferably penicillin and streptomycin. The medium also contains serum, preferably non-heat treated human AB serum at a concentration of 10%. Serum should be tested for antibodies to the virus of choice. For example, when the MDM cultures are to be infected or reactivated with HCMV, the serum should be free of virus (HCMV) and antibodies to the virus.

After a culture under standard conditions for a suitable time, preferably approximately 48 hours, the cells are. washed to remove non-adherent cells (e.g., B and T cells). At this point the monocytes have adhered to the culture substrate. The cultures are then maintained in media that is composed of approximately 50% spent media:50% fresh media. The media used after adherence is typically a mix of proliferative media such as AIM-V (GIBCO), and adherence media such as Iscove's. The ratio of the media is not critical. Preferably, the media is 60% proliferative media (e.g., AIM-V) and 30% adherence media (Iscove's). The media is replenished approximately every 3–4 days, and the cultures can be maintained minimally up to 90 days post-stimulation. After adherence, the cultures have a cell density of approximately $10^4-10^6$ cells per ml.

MDM cultures are either examined for reactivation of latent virus approximately 22–26 days after allogeneic stimulation, or infected with exogenous virus approximately 8–10 days after allogeneic stimulation. For infection with exogenous virus stocks, typically a multiplicity of infection ("MOI") from 1–100 is used to infect the cells (see, e.g., Example I). The cells are then cultured under standard conditions and examined for the presence of virus, as described below. The cells infected with exogenous virus or reactivated virus are compared to non-infected cultures and non-virally permissive cultures. Typically, the virally permissive cultures of the invention produce at least about 10,000 fold greater virus than non-permissive cells. Mammalian viruses for infection or reactivation of MDM cultures include, e.g, HCV, HHV6, HHV7, HHV8, HIV, and HCV. Virus stocks are obtained from commercially available sources, the ATCC, or patient isolates (e.g., HCMV isolates PO and PE, Example I). Viral stocks are titered and maintained according to standard procedures (see, e.g., Ausubel et al., supra; Sambrook et al., supra; Example I).

B. Cell Culture

In general, the cell culture environment includes consideration of such factors as the substrate for cell growth, the gas phase, the medium, and temperature. For cells such as monocytes that grow in a monolayer attached to a substrate, typically plastic dishes or flasks are used. Other artificial substrates can be used such as glass and metals. The substrate is often treated by etching, or by coating with substances such as collagen, chondronectin, fibronectin, and laminin. The type of culture vessel depends on the culture conditions, e.g., multi-well plates, petri dishes, tissue culture tubes, flasks, and the like. Cells are grown at optimal densities that are determined empirically based on the cell type. For example, before adherence, a typical cell density for MDM cultures varies from $1\times10^6$ to $1\times10^8$ cells per ml of medium, and after adherence the typical cell density is approximately $1\times10^4-1\times10^6$ cells per ml.

Important constituents of the gas phase are oxygen and carbon dioxide. Typically, atmospheric oxygen tensions are used for MDM cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1–10% in the incubator. The preferred $CO_2$ concentration for allogeneic stimulation and MDM culture is 5%.

Cultured cells are normally grown in an incubator that provides a suitable temperature, e.g., the body temperature of the animal from which is the cells were obtained, accounting for regional variations in temperature. Generally, 37° C. is the preferred temperature for MDM cell culture. Most incubators are humidified to approximately atmospheric conditions.

Defined cell media are available as packaged, premixed powders or presterilized solutions. Examples of commonly used media include Iscove's media, AIM-V, RPMI 1640, DMEM, and McCoy's Medium (see, e.g., GibcoBRL/Life Technologies Catalogue and Reference Guide; Sigma Catalogue). Iscove's complete media is preferred for pre-adherence cultures, and mixed proliferative and adherence media are preferred for post-adherence cultures. Defined cell culture media are often supplemented with 5–20% serum, e.g., human horse, calf, and fetal bovine serum. The preferred serum for allogeneic stimulation and MDM culture is 10% non-heat inactivated human AB serum (Sigma). The culture medium is usually buffered to maintain the cells at a pH preferably from 7.2–7.4. Other supplements to the media include, e.g., antibiotics, amino acids, sugars, and growth factors.

V. Detection and Characterization of Virus in Cultured Monocyte-derived Macrophages After the cell of choice, e.g., PBMC or monocyte, has been allogeneically stimulated and differentiated into MDM in a stable culture, the cells are examined for their permissiveness for viral reactivation and infection. The MDM cultures are typically used to examine reactivation of latent infections such as HCMV. Macrophages that express dendritic cell markers may also constitute reservoirs for latent viruses other than HCMV.

Alternatively, the cultures are also useful for studying exogenous viral infection. The cultures of the invention are suitable for studying many types of mammalian viruses that infect and replicate in monocyte-derived macrophages, e.g., HCMV (human cytomegalovirus), DNA viruses of the herpes family; HHV6, HHV7, and HHV8 (human herpes virus 6, 7, and 8), a DNA virus of the herpes family that is associated with Kaposi's sarcoma); HCV (hepatitis C virus), an RNA virus of the flavivirus family; and HIV (human immunodeficiency virus), an RNA virus of the lentivirus family.

Infection of MDM with a virus can be examined using a variety of techniques. The genome and transcripts of the virus are detected using nucleic acid hybridization and amplification techniques. Viral proteins and particles are detected using any one of a number of immunological techniques known to those skilled in the art. Viral titers and infectivity are examined by isolating supernatant from infected cells, and then infecting other cells with the virus. For example, cells such as human fibroblasts are commonly used to determine viral titers using serial dilutions and plaque forming assays.

These techniques to detect viral infection of MDM are used for many applications. Detection of virus genome sequences is useful for diagnosing latent infection. Detection of viral transcripts, proteins, and particles are useful for examining the effect of inhibitors of viral production. Detection of viral genomes, transcripts, proteins, and particles is also useful for studying the life cycle of a virus in vitro.

A. Nucleic Acid Detection

Techniques used to detect viral DNA and RNA from the cells of the invention include a wide variety of techniques based on nucleic acid hybridization e.g., northern blots, Southern blots, dot blots, DNA fingerprinting, RNase protection, and filter hybridization. One variation of nucleic acid hybridization techniques includes those based on nucleic acid amplification, such as reverse transcription ("RT"), polymerase chain reaction ("PCR"), ligase chain reaction ("LCR"), and nucleic acid sequence-based amplification ("NASBA"). Detectable moieties used in these methods include, e.g., labeled polynucleotide probes, direct incorporation of label in amplification or RT reactions, and labeled polynucleotide primers.

Nucleic acid probes and primers used for hybridization assays are chosen to hybridize to a target viral gene or transcript. The probe can be a DNA or RNA molecule, as well as a synthetic, non-naturally occurring analogue of the same. Hybridization conditions are selected by those skilled in the art, as discussed herein. Although primers and probes can differ in sequence and length, the primary differentiating factor is one of function: primers typically serve as an initiation point for DNA synthesis of a target nucleic acid, as in RT and PCR reactions, while probes are typically used for hybridization to and detection of a complementary target nucleic acid. Typical lengths of primers or probes can range from about 7 to about 50 nucleotides. A rimer or probe can also be labeled with a detectable moiety for detection of hybridization of the primer or probe to the target nucleic acid.

One preferred hybridization assay is reverse transcription. Reverse transcription is an amplification method that copies RNA into DNA. The reverse transcription reaction, which synthesizes first strand cDNA, is typically performed by mixing RNA with random hexamer primer or a specific primer, heating to 70° C. for 5 minutes to denature the nucleic acids (a thermal cycler may be used for this step), and then cooling on ice. The reaction mixture, prepared according to the enzyme manufacturers instructions or according to kit instructions, is added to the denatured RNA and hexamer mixture and incubated at a suitable temperature, usually 42° C. The reaction is stopped by heating the tube containing the reaction mixture for 10 minutes at 70° C. The first strand cDNA is collected by precipitation and brief centrifugation and aliquoted to new tubes, in which it can be quickly frozen on dry ice and stored at −70° C., if necessary, for later use.

Another preferred type of hybridization assay are amplification based assays such as PCR (polymerase chain reaction) and LCR (ligase chain reaction). Standard techniques for performing such assays are known in the art (*PCR Technology: Principles and Applications for DNA Amplification* (Erlich, ed., 1989); *PCR Protocols: A Guide to Methods and Applications* (Innis, Gelfland, Sninsky, & White, eds., 1990); Mattila et al., *Nucleic Acids Res.* 19:4967 (1991); Eckert & Kunkel, *PCR Methods and Applications* 1:17 (1991); Wallace et al., *Ligase Chain Reaction, in Technologies for Detection of DNA Damage and Mutations*, pp. 307–322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., supra).

For example, PCR is typically carried out in a buffered aqueous solution, preferably at a pH of 7–9. Deoxyribonucleoside triphosphates are added to the synthesis mixture in adequate amounts, and the resulting solution may be heated to about 85–100° C. for about 1 to 10 minutes. After this optional heating period, the solution is allowed to cool to about 20–40° C., for primer hybridization. An agent for polymerization is added to the mixture, and the reaction is allowed to occur under conditions known in the art, typically using a thermocycler. This synthesis reaction may occur at room temperature up to a temperature just over which the agent for polymerization no longer functions efficiently. The agent for polymerization may be any compound or system that will function to accomplish the synthesis of primer extension products, including enzymes. Suitable enzymes for this purpose include, for example, *E. coli* DNA polymerase I or Klenow fragment, Taq DNA polymerase, and other available DNA polymerases.

A final preferred method of detecting the presence of viral genome sequences is Southern hybridization. Briefly, DNA is isolated from a cell and digested with restriction enzymes. The digested DNA is run on agarose slab gels in buffer and transferred to membranes. Hybridization to the membrane is carried out using labelled probes which specifically hybridize to viral nucleic acids (see, e.g., Ausubel et al., supra; Sambrook et al., supra; Example III).

Cells that are infected by virus can also be identified by in situ hybridization. A sample of tissue or cells is fixed onto a glass slide and permeablized sufficiently for use with in situ hybridization techniques, according to standard methods. After the sample is fixed, a primer that specifically hybridizes to the viral nucleic acid of choice is hybridized to the sample, and then the hybridization of the primer is detected, for example, using an RT-PCR protocol or other methods described herein.

These methods of detecting hybridization, described above, generally include the use of a detectable moiety. Primers and probes that include detectable moieties are synthesized by standard methods known to those skilled in the art (see Ausubel, et al., and Sambrook, et al., supra). The detectable moiety may be directly or indirectly detectable and associated with either a primer or a probe. Directly detectable moieties include, e.g., polynucleotides that are labeled with $^{32}P$ at the 5' end of the molecule, or that incorporate radioactive nucleotides. Indirectly detectable moieties include, for example, polynucleotides that incorporate biotinylated nucleotides recognized by streptavadin, or a nucleotide sequence, which is the binding partner for a radioactively labeled complementary sequence.

The detectable moiety often generates a measurable signal, such as a radioactive, chromogenic, or fluorescent signal, that can be used to quantitate the amount of bound detectable moiety, for example, for measuring the ability of a substance to inhibit viral production. Quantitation of the signal is achieved by methods known to those skilled in the art, for example, scintillation counting, densitometry, or flow cytometry.

Oligonucleotides preferably are synthesized on an Applied BioSystems or other commercially available oligonucleotide synthesizer according to specifications provided by the manufacturer. Oligonucleotides may be prepared using any suitable method, such as the phosphotriester and phosphodiester methods, or automated embodiments thereof. In one such automated embodiment, diethylphosphoramidites are used as starting materials and may be synthesized as described by Beaucage et al., *Tetrahedron Letters* 22:1859 (1981), and U.S. Pat. No. 4,458,066.

Nucleic acids, e.g., probes, also can be recombinantly produced through the use of plasmids or other vectors. Vectors can be adapted for function in prokaryotes or eukaryotes by inclusion of appropriate promoters, replication sequences, selectable markers, etc. for replication and transcription of a nucleotide sequence. The construction of vectors and the replication and expression of genes in transfected cells involves the use of molecular cloning techniques also well known in the art (see, e.g., Ausubel et al., supra; Sambrook et al., supra; Berger & Kimmel, volume 52, *Methods in Enzymology, Guide to Molecular Cloning Techniques* (1987)). The particular vector used to transport the genetic information into the cell is also not particularly critical. The vector containing the sequence of interest is transformed into host cells for replication and expression. The particular procedure used to introduce the genetic material into the host cell is not particularly critical. It is only necessary that the particular procedure utilized be capable of successfully introducing at least one gene into the host cell which is capable of expressing the gene (see generally Sambrook et al., supra; Ausubel, et al., supra.

B. Immunological Detection of Viral Proteins and Cell Surface Markers

In addition to the detection of viral genes and gene expression using nucleic acid hybridization technology, one can also use immunoassays to detect viral proteins and to measure inhibitory activity of substances being tested for their ability to inhibit viral production. Immunoassays can be used to qualitatively or quantitatively analyze viral protein production in infected cells, e.g., in assays for substances that inhibit viral production. A general overview of the applicable technology can be found in Harlow & Lane, *Antibodies: A Laboratory Manual* (1988).

1. Antibodies to Viral Proteins

Methods of producing polyclonal and monoclonal antibodies that react specifically with viral proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495–497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of viral protein immunogens may be used to produce antibodies specifically reactive with viral proteins. For example, recombinant viral proteins or a antigenic fragments thereof can be isolated, expressed in eukaryotic or prokaryotic cells, and purified as generally described above. Recombinant protein is the preferred immunogen for the production of monoclonal or polyclonal antibodies. Alternatively, a synthetic viral peptide can be conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein. Suitable viral proteins for use as antigens include herpes virus (e.g., HHV6–8 and CMV) major intermediate early protein and glycoproteins gB, gD and gH; HIV glycoprotein gp120, phosphoprotein p24, RT, and protease; HCV glycoproteins E1 and E2, and structural protein C.

Methods of production of polyclonal antibodies are known to those of skill in the art. An inbred strain of mice or rabbits is immunized with the protein using a standard adjuvant, such as Freund's adjuvant, and a standard immunization protocol. The animal's immune response to the immunogen preparation is monitored by taking test bleeds and determining the titer of reactivity to the viral antigen of choice. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-viral proteins or even other homologous proteins from other organisms, using a competitive binding immunoassay. Specific polyclonal antisera and monoclonal antibodies will usually bind with a $K_D$ of at least about 0.1 mM, more usually at least about 1 $\mu$M, preferably at least about 0.1 $\mu$M or better, and most preferably, 0.01 $\mu$M or better.

Once viral specific antibodies are available, viral proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

2. Immunological Binding Assays

Expression of viral proteins is a signal of infection or reactivation of a latent infection. Inhibition of viral production can also be measured by monitoring the level of expression of viral proteins. Viral proteins therefore can be detected and/or quantified using any of a number of well recognized immunological binding assays (see, e.g., U.S. Pat. No. 4,366,241; 4,376,110; 4,517,288; and 4,837,168). For a review of the general immunoassays, see also *Methods in Cell Biology Volume 37: Antibodies in Cell Biology* (Asai, ed. 1993); *Basic and Clinical Immunology* (Stites & Terr, eds., 7th ed. 1991). Immunological binding assays (or immunoassays) typically utilize a "capture agent" to specifically bind to and often immobilize the analyte (in this case the viral protein or antigenic subsequence thereof). The capture agent is a moiety that specifically binds to the analyte. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled viral polypeptide or a labeled antibody. Alternatively, the labeling agent may be a third moiety, such as another antibody, that specifically binds to the antibody/antigen complex.

In one embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see generally Kronval, et al., *J. Immunol.*, 111:1401–1406 (1973); Akerstrom, et al., *J. Immunol.*, 135:2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting viral protein in samples may be either competitive or noncompetitive. Noncompetitive immunoassays are assays in which the amount of captured analyte (in this case the protein) is directly measured. In one preferred "sandwich" assay, for example, the capture agent (anti-viral protein antibodies) can be bound directly to a solid substrate on which they are immobilized. These immobilized antibodies then capture viral proteins present in the test sample. Viral protein is thus immobilized is then bound by a labeling agent, such as a second viral protein antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the amount of viral protein (analyte) present in the sample is measured indirectly by measuring the amount of an added (exogenous) analyte displaced (or competed away) from a capture agent (anti-viral protein antibody) by the analyte present in the sample. In one competitive assay, a known amount of, in this case, the viral protein of choice is added to the sample and the sample is then contacted with a capture agent, in this case an antibody that specifically binds to the viral protein of choice. The amount of viral protein bound to the antibody is inversely proportional to the concentration of viral protein present in the sample. In a particularly preferred embodiment, the antibody is immobilized on a solid substrate. The amount of the viral protein bound to the antibody may be determined either by measuring the amount of viral protein present in an antigen/antibody complex, or alternatively by measuring the amount of remaining uncomplexed protein. The amount of viral protein may be detected by providing a labeled viral protein molecule.

A hapten inhibition assay is another preferred competitive assay. In this assay a known analyte is immobilized on a solid substrate and a known amount of antibody is added to the sample. The immobilized analyte is then contacted with the sample containing antigen and antibody. The amount of antibody bound to the immobilized analyte is inversely proportional to the amount of antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Western blot (immunoblot) analysis is used to detect and quantify the presence of viral proteins in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the antigen of choice. The antibodies specifically bind to the antigen on the solid support. These antibodies may be directly labeled or alternatively may be subsequently detected using labeled antibodies (e.g., labeled sheep anti-mouse antibodies) that specifically bind to the primary antibodies.

Other assay formats include liposome immunoassays ("LIA"), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin ("BSA"), nonfat powdered milk, and gelatin are widely used with powdered milk being most preferred.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices ("CCDs") or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Characterization of Virally Permissive Monocyte-derived Macrophages

The immunological and nucleic acid techniques described above can also be used to isolate the virally permissive monocyte-derived macrophages of the invention, using specific cell markers. A variety of methods for purification of cells is known to those skilled in the art. Typically, a physical or functional marker is chosen for use in conjunction with physical separation techniques to isolate the cell. For example, a cell surface molecule is often used with immunological techniques to purify a cell. For example, the virally permissive MDM of the invention express the macrophage cell surface markers CD14 and CD64, and the dendritic cell markers CD68, CD1a and CD83. Latent infection with HCV is another suitable marker. Alternatively, the functional characteristic of viral permissiveness can be used to isolate the MDM. For the MDM of the invention, the cell surface markers CD14 and CD83 provide a convenient physical marker for isolation. Antibodies to CD14 and CD83 are therefore used to identify the cell (see Example IV for additional antigens used as markers) Antibodies to CD14, CD83 and other cell surface antigens are commercially available.

As described above, a number of techniques are known to those skilled in the art to bind an antibody to an antigen. The cell bound by the antibody may or may not be labeled. Once the antibody has bound the cell, physical separation techniques are used to separated antibody-bound cells from the rest of the cells in culture. For example, the cells may be passed over an affinity column or subjected to flow cytometry. Other techniques include density gradient centrifugation, immune panning, magnetic activated cell sorting, and electrophoresis in a Ficoll gradient or by curtain electrophoresis (see, e.g., Freshney, supra). After isolation, the purified MDM cells are cultured as described above.

VII. Assays for Viral Reactivation, Viral Inhibitors, and Viral Infection

The present invention provides for the first time stable, virally permissive cultures of monocyte derived macrophages, in which HCMV latent infections can be reactivated. Thus, these cultures can be used to identify substances that inhibit viral production and reactivation of latent infection. The viral production may be, e.g., viruses such as HHV6–8, HIV, and HCV and well as HCMV.

The ability of molecules to inhibit viral production can be assessed using a variety of in vitro assays as described above, e.g., immunoassays and nucleic acid hybridization assays. Inhibitors of viral production are useful as pharmaceutical treatments for mammalian viral diseases, both latent infections and exogenous infections. In particular, inhibitors of viral production can be used to prevent reactivation of a latent virus infection.

Molecules that are potential inhibitors of viral production include antisense nucleic acid, ribozymes, small chemical molecules, and proteins. Targets for inhibition of viral production include enzymes such as viral polymerases that are involved in replication of the viral genome, viral transcriptional activators, viral proteases such as UL80, UL89, and HIV protease, and components of the viral particle. The inhibitors can target genes, mRNA, and proteins. The inhibitor can be introduced to the cell by a variety of methods, including transfection, electroporation, infection, lipofection, passive diffusion, lipid solubility, and active transport.

Cell samples or assays that are treated with a potential viral production inhibitor are compared to control samples without the inhibitor, to examine the extent of inhibition. Typically, a culture of MDM is infected with exogenously added virus or latent virus. In parallel with a control uninfected culture, the cell samples are treated with potential inhibitors, incubated for a suitable period of time, and then examined for viral products. Control samples (untreated with inhibitors) are assigned a relative viral production activity value of 100. Inhibition of viral production is achieved when the viral production activity value relative to the control is about 75, preferably 50, more preferably 25.

To determine the efficacy of an inhibitor of viral production, cells are assayed for the presence of viral gene expression products. Detection of viral transcription, viral protein expression, and viral particles can be performed using the nucleic acid and immunological techniques described above.

As described above, characterization of viral infection is also a useful diagnostic tool in vitro. During latent infections, typically the viral genome is partially or wholly repressed. Thus, cells that harbor the viral genome must be identified and then examined either for their ability to reactivate the latent infection, or for the presence of viral genome sequences. The culture methods of the invention and assays described above provide a means of isolating cells that are potentially latently infected with a virus such as HCMV and examining the cells to determine whether or not they are infected.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I:

Generation of Macrophages from PBMC by Allogeneic or Mitogeneic Stimulation Results in Altered Growth of HCMV Methods A. Establishment of Allogeneically Stimulated PBMC Cultures For preparation of allogeneically stimulated MDM ("Allo-MDM"), PBMC were isolated from blood samples of 32 healthy blood donors by density gradient centrifugation on HISTOPAQUE® (Sigma Chemical Co.) as previously described (Fish et al., 1995). Subsequently, PBMC were resuspended in Iscove's complete medium containing penicillin (100 IU/ml), streptomycin (100 μg/ml, both from GIBCO Laboratories) and 10% human AB serum (Sigma Chemical Co., non-heat inactivated, anti-CMV negative). For allogeneic stimulation experiments, equal numbers of cells from two different blood donors at a cell concentration of $1.8 \times 10^7$ cells per ml were mixed before plating Primaria dishes (Becton Dickinson). After 48 hours of culture at 37° C. in 5% $CO_2$, non-adherent cells were removed. Cultures were washed and maintained in media composed of 50% spent media/50% fresh media which was replenished every 3–4 days up to 90 days post-stimulation. Control cell cultures were established by stimulation of PBMC from individual donors with concanavalin A as previously described (Fish et al., J. Virol. 70:1855–1862 (1996)). Day 1 post stimulation is defined as the day after the initial PBMC isolation and allogeneic or Con A stimulation. Donors for latent HCMV reactivation were HCMV positive, donors for culture for exogenous virus were seronegative for that virus.

Cultures were also established using a transwell system. In this system, PBMC from two donors were mixed and placed in the outside well. PBMC from one of the donors or a third donor were placed in the inside well, which has a 0.45 micron membrane at the bottom. This membrane allows the PBMC in the two compartments to remain in fluid communication. After 48 hours, the cells in the inner well were plated and washed to establish the MDM cultures.

B. HCMV Infection of MDM Cultures

Two recent patient isolates of HCMV were used to infect primary cultures of MDM. These isolates (PO and PE) were isolated from transplant patients with HCMV disease. Cell free viral stocks which were stored at $-70°$ C. were prepared from supernatants of infected human fibroblast ("HF") cultures. Viral strains used in experiments were passaged less than 15 times in HF cells. MDM cultures were infected with HF supernatants at a multiplicity of infection ("MOI") of 1–10 at 8 to 10 days post allogeneic stimulation or stimulation with Con A. For mock infection, cells were exposed to media from uninfected HF cultures. The cultures were fed every third day, and collected for viral titer assays at different time points after infection.

C. Immunocytochemistry

HCMV infected and mock infected MDM cultures grown in 8-well chamber slides or in Primaria 96 well plates were collected at different time points after infection. The cells were washed in PBS and fixed in phosphate buffered 1% paraformaldehyde ("PFA") or methanol/acetone (1:1) for 10 minutes at room temperature and permeabilized with 0.3% Triton X-100 in PBS. Cells were blocked with 10% normal goat serum or 10% human AB serum in PBS for 30 minutes at room temperature, and thereafter with antibodies against different HCMV gene products in a 1:100 dilution for 1–6 hours at room temperature: antibodies against the major immediate early protein (rabbit-anti-MIE (Stenberg et al., J. Virol. 63:2699–2708 (1989)), or gB (mouse-anti-gB (UL55)). Both murine monoclonal antibodies were a gift from Dr. William Britt at the University of Alabama, Birmingham, Ala. (Britt & Vugler, J. Virol. 66:6747–6754 (1992)).

Cells were washed three times in PBS and binding of the primary antibody was detected with a fluorescein isothiocyanate-tetramethyl ("FITC") conjugated goat anti-mouse or goat anti-rabbit antibody for 1–2 hours at room temperature. Double immunocytochemistry for cell surface markers was performed on live cells before fixation and staining for the HCMV IE antigen was performed. Stained cells were washed in PBS and mounted in Slow fade Antifade Kit (Molecular Probes Inc., Eugene, Oreg.) to ensure minimal fluorescence fading. Fluorescence positive cells were visualized on an upright or inverted Leitz fluorescent microscope and the number of infected cells was counted.

D. Dendritic Cell Culture

PBMC were isolated as described above and plated onto primaria plates for monocyte adherence. After two hours of culture, non-adherent cells were removed by three washes in serum free medium and adherent cells were stimulated with I1–4 (1000 U/ml) and GM-CSF (50 ng/ml) as previously described (Sallusto et al., *J. Exp. Med.* 179:1109–1118 (1994)). Immature dendritic cells cultured in RPMI medium containing 1% sodium pyruvate were developed during the first 12 days of culture. Cell samples were collected at 12 days for flow cytometric analysis to determine the expression of dendritic and macrophage markers. Small, round dendritic cells were stimulated with TNF-γ (10 ng/ml), IFN-γ (500 U/ml), or TNF-γ (10 ng/ml) and IFN-γ (500 U/ml) for two days. Thereafter, the mature, adherent dendritic cells were challenged with HCMV at a MOI of 10 or mock infected as described herein.

Results

A. Exogenous Infection with HCMV

Characteristics of viral replication were compared in macrophages generated by concanavalin A-stimulated PBMC ("Con A-MDM") or Allo-MDM. HCMV infection of Allo-MDM at a multiplicity of infection ("MOI") of 10 resulted in a rapid lytic infection of cells. Cytopathic effects ("CPE") were first detectable at 3 days post infection ("dpi") and >80% lysis of infected Allo-MDM was observed at 7 dpi. Infection at an MOI of 1 was non-lytic over an observation period of 20 days. In contrast, HCMV infection of Con A-MDM was non-lytic at intervals up to 90 dpi at MOI >10.

B. Detection of Viral Production

To examine the kinetics of HCMV replication in Allo-MDM, in vitro infected cultures were monitored for production of infectious virus at a variety of time points. The kinetics of HCMV replication in Allo-MDM was rapid and significant quantities of virus were found in both the cellular and extracellular fractions. These characteristics are similar to viral replication in fibroblasts which are the prototypic cell for growing HCMV in vitro. In comparison, viral replication in the Con A-MDM was delayed, exhibited lower levels of viral production, and virus was only found associated with the cellular fraction.

The importance of allogeneic stimulation for unrestricted HCMV replication in Allo-MDM was demonstrated by the lack of viral replication in cultures derived by mixing PBMC from HLA identical twins. The frequency of HCMV infected Allo-MDM was assessed by the detection of the immediate early ("IE") as well as the late glycoprotein B ("gB") antigen by immunofluorescence. In contrast to the low numbers (<10%) of cells expressing viral antigens in the Con A-MDM cultures, greater than 50% of the Allo-MDM expressed both IE and gB antigens at 12 dpi. In addition, the kinetics of expression of the structural protein gB correlated with the rapid production of virus within Allo-MDM. These observations demonstrate a highly altered vigorous growth of HCMV in the macrophage generated by the allogeneically driven differentiation process in comparison to mitogeneically differentiated MDM.

Allo-MDM express both macrophage (CD14and CD64) and dendritic cell (CD83 and Cd1a) markers, in contrast to ConA MDM, which express only macrophage markers (CD14and CD64). Since some dendritic cells may be related to the Allo MDM, HCMV replication was examined in dendritic cells. Monocyte derived dendritic cells (MDDC) were obtained through treatment of monocyte enriched cultures with IL-4 and GM-CSF. The MDDC expressed the dendritic cell markers CD1a and CD83 but not the monocyte/macrophage markers CD14and CD64. HCMV in vitro infection of MDDC resulted in IE expression in 25–45% of the cells at 1 dpi. However, neither IE or late viral antigens were detected past this interval up to 20 dpi. Additional stimulation of MDDC with IFN-γ or TNF- to obtain mature DC did not increase viral expression beyond what was observed in the unstimulated cells up to day 12 post stimulation. These results indicate that although Allo-MDM, ConA-MDM, and MDDC are all derived from $CD14^+$ monocytes, HCMV displays differential patterns of replication in each of these different cell types.

Example II

Generation of Allo-MDM is Mediated by Cytokines IFN-γ and $CD4^+$ and $CD8^+$ T cells Methods

A. Negative Selection of PBMC Subpopulations

In order to obtain $CD4^+$ or $CD8^+$ T cell depleted Allo-MDM cultures, the Mini MACS system (Miltenyi Biotec, Bergish Gladbach, Germany) was used for negative selection of the respective cell type. Freshly isolated PBMC were stained with monoclonal antibodies directed against $CD4^+$ T cells (anti-human Leu-3a), $CD8^+$ T cells (anti-human Leu-2a, both from Becton Dickinson), or isotype control sera (mouse IgG1 Fc, R&D Systems, Minneapolis, Minn.). $1 \times 10^8$ cells in 500 μl serum free Iscove's medium were incubated with a titered excess of the respective antibody at 4° C. for 45 minutes. The cells were washed twice in cold PBS, resuspended in 250 μl of MACS buffer (PBS containing 5 mM EDTA and 0.5% BSA) and incubated with 160 μl MACS beads conjugated with rat-anti-mouse IgG1 antibodies for 20 minutes at 4° C.

Each MACS column was washed with 15 ml of MACS buffer before the addition of the respective sample. PBMC coupled to MACS beads were eliminated from the samples by flow through the column in a magnetic field under flow resistance. Each column was washed with 4 ml MACS buffer, and the collected cells were washed twice in serum free medium, and resuspended in complete 60/30 medium.

Cells from two donors were allogeneically stimulated as described above. Small aliquots of each sample before and after negative selection were analyzed by flow cytometry to ensure satisfactory purity of each sample before the establishment of each Allo-MDM culture.

B. HLA Class I and HLA Class II Blocking Experiments

To block the interaction between T cells and monocytes, monoclonal antibodies directed against constant regions of HLA A, B, C, or HLA-DR (both from Immunotech, Westbrook, Me), or isotype controls (mouse IgG2a or mouse IgG2b, both from R&D Systems) at a concentration of 35 μg/ml were preincubated with $7 \times 10^7$ cells in Iscove's complete medium for 1 hour at 4° C. before allogeneic stimulation. Thereafter, non-adherent cells and antibodies in the cultures were removed by three washes in serum-free medium, and the Allo-MDM cultures were cultured in complete 60/30 medium for up to 30 days.

C. Neutralization of Cytokines in Allo-MDM Cultures

For neutralizing experiments, polyclonal neutralizing goat antibodies against human GM-CSF, IL-1, IL-2, TGF-α or IFN-α (R&D Systems) were used to block the respective cytokine produced in MDM cultures. Antibodies were added to the cultures at the same time as allogeneic stimulation, and were present in the cultures for 48 hours post stimulation. Thereafter, non-adherent cells and antibodies in the cultures were removed by three washes in serum-free medium, and the Allo-MDM cultures were cultured in complete 60/30 medium for up to 30 days.

D. Addition of Cytokines to Standard Dendritic Cell Cultures

PBMC were cultured under standard conditions with IL-4 and GM-CSF to yield monocyte-derived dendritic cells (see, e.g., *Annals Surg.* 226:1–5 (1997)). The dendritic cells were infected in vitro under the conditions described herein with HCMV. Some cultures were then treated by the addition of TNF-α and IFN-γ, separately and together, to examine the effects of the cytokines on viral growth in cells cultured using these standard methods. Viral growth is measured as described with antibodies against viral proteins IE and gB. Viral growth is measured at days 1, 3, 8, 12, and 20 post infection.

Results

A. Depletion of $CD4^+$ T Cells, $CD8^+$ T Cells, and MHC molecules from PBMC To identify the cellular elements within the PBMC population which are important for the development of HCMV-permissive Allo-MDM, $CD4^+$ or $CD8^+$ T cells were depleted from PBMC using a negative selection technique. For these experiments, the respective cell type was eliminated from the PBMC of each donor prior to the establishment of Allo-MDM cultures. Flow cytometric analysis was performed on cells before and after negative selection to ensure that the residual cell phenotype was less than 3%. Depletion of either $CD4^+$ or $CD8^+$ T cells from the PBMC before virus challenge resulted in a 90% reduction in the number of Allo-MDM expressing IE proteins as well as a 3–4 log decrease in the production of virus.

The addition of neutralizing antibodies directed against HLA class I or HLA class II to PBMC prior to allogeneic stimulation also resulted in a 3–4 log decrease in virus.

These experiments demonstrate that the generation of HCMV-permissive Allo-MDM by an allogeneic reaction involves both $CD4^+$ and $CD8^+$ T cells as well as HLA class I and II molecules. The ability of antibodies directed against HLA class I and II to block formation of HCMV permissive Allo-MDM also demonstrates that T cell contact is necessary for the specific differentiation of these cells.

Similar experiments with Con A-MDM indicated that depletion of $CD8^+$ but not $CD4^+$ T cells and neutralization of HLA class I but not HLA class III molecules significantly decreased viral titers in MDM. These observations suggest that $CD8^+$ T cell contact with the monocyte through the HLA class I pathway is important in the generation of both the Allo-MDM and the Con A-MDM. Therefore, the critical difference between the two systems is the differentiation of monocytes by a $CD4^+$ T-cell mediated mechanism for the development of HCMV permissive Allo-MDM.

B. Depletion of Cytokines from Allo-MDM Cultures

In order to determine if specific cytokines mediated the reactivation of latent HCMV in permissive Allo-MDM, polyclonal antibodies with neutralizing activity to IL-1, IL-2, TNF-α, GM-CSF, or IFN-γ were added separately to Allo-MDM cultures. Neutralization of IFN-γ, in Allo-MDM cultures resulted in an significant reduction in cells expressing viral antigens IE and gB, as well as in a 4 log reduction in the production of infectious virus. Furthermore, neutralization of Il–2 appeared to result in reduction of the number of infected cells. Neutralization of the remainder of the cytokines listed above did not affect the ability of the cultures to reactivate latent HCMV. This data indicates that IFN-γ in particular is required for growth of latent virus in Allo-MDM. This data also indicates that the Allo-MDM are a new cell type, since their differentiation does not appear to be affected by the removal of GM-CSF. In contrast, neutralization of TNF-γ decreased viral titers in infected ConA-MDM.

C. Reactivation of Latent HCMV and Cytokine Depletion

Allogeneically stimulated cell cultures were established to determine whether additional cytokines are required for reactivation of latent virus. Donors were tested for HCMV exposure by ELISA for serum antibodies and by PCR for the presence of HCMV DNA in PBMC. As described above, neutralizing antibodies were added to the cultures. HCMV IE proteins were detected at day 14–21 post infection without the addition of neutralizing antibodies, and the late HCMV gB antigen was detected in adherent cells between days 21 and 35 post stimulation. At day 52 post stimulation IE positive cells were quantified. Neutralization of IFN-γ but not IL-1, IL-2, TNF-γ, TGF-β, or GM-CSF for the first 48 hours post stimulation resulted in 80–95% reduction in the number of HCMV positive Allo-MDM. These results indicate that reactivation of latent HCMV in Allo-MDM is dependent on IFN-γ production.

D. Monocyte-derived Dendritic Cell Cultures

Monocyte-derived dendritic cells were cultured under standard procedures via stimulation with IL-4 and GM-CSF. These cells are a different differentiated cell type than monocyte-derived macrophages. After approximately 8 days, the dendritic cells were infected with exogenously added HCMV as described herein. The cells were not permissive for HCMV growth, as demonstrated by the lack of expression of viral antigen (see above). Neutralization of TNF-α and IFN-γ had no effect on the culture's viral permissiveness.

Example III

Reactivation of Latent HCMV from All o-MDM Obtained from Healthy Blood Donors and Characterization of HCMV Methods

A. Virus Titer Assays

Supernatants from MDM cultures were collected at different days post infection, and MDM were harvested by scraping adherent cells into DMEM medium containing 2% fetal bovine serum ("FBS"), 2 mM L-glutamine, 100 IU/ml penicillin and 100 μg/ml streptomycin. Supernatants or sonicated MDM cells were plated onto monolayers of HF cells at subconfluency. After an initial 24 hours of viral adherence at 37° C., cells were washed twice in medium and overlaid with DMEM medium containing 10% FBS, 2 mM L-glutamine, 100 IU/ml of penicillin, 100 pg/ml of streptomycin, and 0.5% autoclaved SeaKem agarose (Sigma). The cultures were incubated for 14 days, with feeding every fourth day. The cells were fixed with 25% formaldehyde in PBS for 15 minutes, stained with a 0.05% solution of methylene blue, and plaques were counted (Wentworth & French, Proc. Soc. Exper. Biol. & Med. 135:253–258 (1970)).

B. Detection of HCMV Replication in Allo-MDM

Allo-MDM cultures were established by mixing PBMC from two healthy blood donors as described above. Samples were collected at day 1, 10, 17, 26, 36, 46, 54, 60, 70, 80 and 90 for detection of HCMV gene products, and/or for virus recovery. Sonicated cells were plated onto HF (human fibroblast) cells at subconfluency in 96 well plates or in 25 cm$^2$ culture flasks for virus isolation. HF cells in 96 well plates were incubated for 17–20 days with feeding every fourth day, fixed and stained for the presence of HCMV IE antigens using a polyclonal antibody against IE (Fish et al., J. Virol. 69:3737–3743 (1995)).

For PCR analysis, cell samples were collected at the indicated time points by scraping. DNA and RNA were prepared using the QIAGEN Blood and the Cell culture DNA kit and RNeasy kit, respectively, according to the manufacturer instructions. HCMV specific primer pairs were used in nested RT-PCR reactions detecting IE and pp150 RNA (Ssderberg et al., 1993). As a positive control for the presence of DNA or RNA primers detecting glucose-6-phosphatase dehydrogenase ("G6PD") were used for each sample (Ssderberg et al., J. Virol. 67:3166–3175 (1993)). The primers used for PCR analysis for HCMV IE and G6PD span an intron and yield different sized bands from amplification of DNA and RNA, whereas the pp150 gene does not contain an intron and yield DNA and RNA PCR products of the same size. The PCR products were visualized by direct gel analysis on a 1% agarose gel.

Experiments to detect the expression of HCMV proteins in Allo-MDM as well as double label experiments to co-localize viral and cellular proteins utilized immunofluorescence in combination with confocal microscopy as described under immunocytochemistry.

C. Infection of Human Fibroblast Cells and Southern Analysis

Cell free viral stocks of the laboratory HCMV strains AD169, Towne as well as a clinical isolate obtained from a bone marrow transplant patient with acute HCMV disease or cell sonicates from Allo-MDM from the respective donor pairs, were used to infect HF cultures. DNA was prepared from HF when a cytopathic effect was observed (10–16 weeks for the reactivated strains versus 7–9 days for the laboratory strains). 10 μg of total DNA from uninfected HF cells was digested with EcoRI or HindIII, before Southern blot analyses using $^{32}$P labelled cosmid clones pCM1058 and pCM1048 and pCM1039 (Fleckenstein, B. et al., Gene, 18, 39–46 (1982)).

Results

Since HCMV frequently reactivates in recipients of allogeneic blood transfusions, organ or bone marrow transplants and the virus exhibits an altered growth in Allo-MDM during in vitro infection, virus was examined to see if it could be reactivated from its latent state in allogeneically stimulated PBMC obtained from naturally infected healthy blood donors.

A. Allo-stimulation of PBMC and HCMV Reactivation

Donors were tested for HCMV exposure by ELISA for serum antibodies and by PCR for the presence of HCMV DNA in PBMC. Allogeneically stimulated cell cultures were established by mixing PBMC from histoincompatible donor pairs (as described above in methods). After 48 hours of allogeneic stimulation, non-adherent cells were removed from the culture and Allo-MDM were maintained with feeding every four days for up to 90 days.

B. HCMV Gene Expression in Allo-MDM

Cell samples were collected from these cultures at the indicated intervals and evaluated for HCMV gene expression by RT-PCR. The presence of HCMV-specific proteins in the Allo-MDM was detected by immunofluorescence and virus production was assessed by co-culture of sonicated cell samples with human fibroblasts ("HF"). HCMV immediate early ("IE") RNA was first detected at day 17 post stimulation in 5/5 allogeneically stimulated cultures. A transcript encoding a late tegument protein pp150 was also observed at day 17 in 4/5 cultures. Interestingly, in one donor pair (donor pair B) the expression of pp150 was not detected until 54 days post allogeneic stimulation.

Consistent with HCMV RNA expression, the IE protein and the late protein gB were detected in adherent cells between days 17 and 60 post stimulation. Failure to detect HCMV transcripts and protein in the Allo-MDM prior to day 17 indicates that the virus is latent and not persistent in this cell population. The frequency of Allo-MDM containing HCMV proteins was 1–12/1000 (0.1–1.2%) when viral antigens were first detected in each culture. By day 60 post stimulation, between 2–25% of the cells expressed HCMV proteins in the different Allo-MDM cultures. The high number of infected cells in some of the cultures at this interval most likely reflects reinfection of Allo-MDM in vitro with reactivated virus.

C. Infection of Human Fibroblasts with Reactivated HCMV

To demonstrate the presence of infectious virus in Allo-MDM, cells obtained from HCMV-positive donor pair cultures were collected every 7–10 days for up to 90 days post stimulation. Cell samples were sonicated and plated onto HF, and HF infection was verified by immunofluorescence for HCMV IE. Infectious virus was demonstrated by this method in 5/5 of the Allo-MDM cultures at days 26–61 post stimulation. In contrast, when Con A-MDM were derived from the same individual donors by mitogenic stimulation of PBMC, virus could not be detected for up to 90 days post stimulation.

Interestingly, HCMV reactivation was observed in Allo-MDM obtained from two HCMV-seronegative donors (donor pair C). However, one of these donors was HCMV DNA positive, which is consistent with the recovery of virus from this donor pair. The successful reactivation of HCMV in the Allo-MDM but not in the Con A-MDM from the same donors implies a fundamental difference in the differentiation process of PBMC.

Long term virus isolation cultures were established from HF cells inoculated with sonicates of Allo-MDM obtained from different donor pairs to allow recovery and characterization of reactivated infectious HCMV strains. Cytopathic effects were observed in HF cells infected with cell sonicates from 6/7 donor pairs after 10–16 weeks in culture. Reactivated HCMV strains obtained from the Allo-MDM replicated slowly in HF and were extremely cell-associated, similar to HCMV isolates obtained from acutely infected individuals.

D. Restriction Enzyme Analysis of HCMV in Infected Human Fibroblasts

Restriction enzyme analyses were performed on HCMV DNA from HF cells infected with reactivated virus to determine the genotype of each isolate. This analysis demonstrates that the sizes of the fragments obtained from digestion of the H and Hz isolates with HindIII or EcoRI are identical. Furthermore, the restriction enzyme analyses also demonstrate that the reactivated virus isolates are distinct from the laboratory isolates AD169 and Towne as well as an isolate obtained from a patient with acute HCMV disease (Po). These experiments clearly demonstrate the unique genotype of the reactivated virus strains.

Example IV

Reactivation of HCMV Occurs in Macrophages that Express Dendritic Cell Markers

Methods

A fluorescence-activated cell analyzer (FACSCalibur; Becton Dickinson) was used for all analyses of cell surface expression using monoclonal antibodies directed against the following cell phenotype markers: CD4, CD8, CD19, CD56, CD13, CD14, CD64, CD1a, CD83, HLA class I molecules, HLA class II molecules, CD40, VCAM-1 and ICAM-1. Mean fluorescence values were obtained from histograms displaying the log fluorescence of FITC ("FL1") or phycoerythrin ("FL2") of the samples which were generated against the background staining of cells stained with an isotype control antibody (mouse IgG1, IgG2a or IgG2b) and the secondary antibody.

For the analysis of purity of the samples prepared by negative selection, histograms were generated displaying the log fluorescence of FITC ("FL1") of the PBMC samples before and after negative selection of CD4, CD8, CD19, CD56 (antibodies were purchased from Becton Dickinson or Dakopatts) positive cells. The percentage of positive cells was estimated by setting the level for positive cells not to include the background staining of uninfected cells in the negative control.

Results

To identify the cell type which reactivated HCMV, Allo-MDM were analyzed by flow cytometry for the expression of specific cell surface markers expressed on T and B cells, NK cells, myeloid cells, and dendritic cells. Control analyses were performed with fresh monocytes and with dendritic cells generated by stimulation of monocytes with recombinant IL-4 and GM-CSF (Sallusto et al., *J. Expt. Med.* 179:1109–1118 (1994)).

Cells staining for T, B and NK cell markers were absent from the adherent cell fraction. The Allo-MDM demonstrated a remarkably uniform surface expression of the monocyte/macrophage markers CD14and CD64 . High levels of expression of the dendritic cell markers CD1a and CD83 were also observed. Co-localization of both CD14and CD83 was consistently observed on Allo-MDM throughout the experimental time course as demonstrated by double label flow cytometric analysis. In contrast, control dendritic cells expressed CD1a and CD83 but were negative for CD14as previously reported (Sallusto, supra).

High levels of HLA class II, HLA class I, CD13, VCAM-1, ICAM-1 and CD40 were observed on the Allo-MDM as well as on monocytes and dendritic cells. The pattern of expression of these markers was consistent in Allo-MDM obtained from the different donor pairs.

An antibody to HCMV was utilized in combination with antibodies to dendritic and macrophage antigens by double label immunofluorescence confocal microscopy to confirm the cellular origin of virus. Cells obtained from donor pair A expressed HCMV IE as well as CD83 and CD14at day 28 post stimulation, but were uniformly negative for HCMV antigens at day 26 post stimulation. Thus, the cells harboring reactivated virus expressed both CD14and CD83.

The above observations provide the first evidence that a myeloid lineage cell in the peripheral blood of healthy individuals is the source of latent HCMV which, upon allogeneic stimulation, reactivates infectious virus. CD14and CD83 double positive cells have previously been reported as a transient cell phenotype during the differentiation of $CD34^+$ hematopoietic progenitor cells stimulated with IL-4 and GM-CSF (Caux et al., *J. Exp. Med.* 184:695–706 (1996)). Since $CD14^+$ cells represent approximately 10% of total PBMC, detection of virus in 1–12 cells/1000 Allo-MDM implies a frequency of HCMV latently infected PBMC of 0.01–0.12%.

Example V

Reactivation of HHV8 after Allogeneic Stimulation of PBMC from HHV8-seropositive Donors Allo-MDM were prepared as described above, using co-cultured PBMC from HHV8 seropositive and seronegative donors. Following eight days of culture, cells were labeled with antibodies to the lytic cycle-associated protein ORF59 (see immunofluorescence methods, described above). Allo-MDM show expression of ORF59. In contrast, ConA-MDM show only expression of latent protein ORF 73, with no expression of lytic cycle proteins.

Example VI

Infection of Allo-MDM by T Cell Tropic and Macrophage Tropic Strains of HIV-1

Allo-MDM were prepared as described above and infected with T cell tropic, macrophage tropic, and dual tropic strains. p24 expression was examined by immunofluorescence, as described above. Allo-MDM were productively infected by each strain.

Example VII

Reactivation of HCMV in $CD14^+$ Monocytes Stimulated with Allo-MDM Conditioned Medium from HCMV Seronegative Donors Using a Transwell System To determine whether cytokines or other soluble factors are sufficient to differentiate monocytes in to HCMV-permissive MDM, allogeneically stimulated MDM conditioned culture medium was used to differentiate $CD14^+$ monocytes obtained from naturally infected seropositive donors. A transwell system was used to separate the monocytes from a single seropositive donor from an allo-reaction of two seronegative donors. PBMCs from the donors were adhered for two hours followed by removal of non-adherent cells. Allo-conditioned medium from parallel cultures was added to the adhered monocytes at 1, 3, 5, and 7 days post-stimulation. Conditioned medium was sufficient to differentiate monocytes into MDM with a similar morphology and viral permissiveness as the parallel Allo-MDM cell cultures. Immunofluorescence was used to identify MDM expressing the HCMV specific proteins IE86 and gB. IE86 and gB positive cells were detected at both 16 and 21 days post-stimulation in MDM from the seropositive donor, but not in MDM from a seronegative donor or from cultures not receiving conditioned medium. These observations indicate that cytokines produce during allogeneic stimulation are sufficient to reactivate HCMV in Allo-MDM.

Example VIII

Cytokine Profiles for Allo-MDM and ConA-MDM

To determine the cytokines produced during culture of virally permissive Allo-MDM, cytokine profiles of Allo- MDM, ConA-MDM and unstimulated macrophages were examined. Culture supernatants were harvested at 6, 12, 24, 36, and 48 hrs. and at 3, 5, and 8 days post-stimulation. The cultures were analyzed using immunoassays as described above (R&D systems) for the following cytokines: IL-1βIL-2, IL-6, IL-7, IL-10, I1–13, GM-CSF, TGF-β, TNF-α, and IFN-γ. Cytokine analysis indicated that substantial differences occurred in the production of these growth factors in Allo-MDM in comparison to ConA-MDM. These results highlight the phenotypic differences between these two monocyte-derived cell types.

What is claimed is:

1. A method of replicating viruses in virally permissive monocyte-derived macrophages, the method comprising the steps of:
   (a) culturing monocytes under conditions where the monocytes are in fluid communication with viable, allogeneically stimulated peripheral blood mononuclear cells (PBMC) to activate the monocytes to differentiate into virally permissive monocyte-derived macrophages; and
   (b) permitting viral replication in the monocyte-derived macrophages, where the virus is either latent in the monocytes or exogenously added to the culture, and wherein the monocyte derived-macrophages have a majority population of cells bearing CD83 and CD14.

2. A method of claim 1, wherein the monocyte derived-macrophages have a majority population of cells bearing CD83, CD68, CD1a, CD64, and CD14.

3. A method of claim 1, wherein the allogeneically stimulated cells include $CD4^+$ and $CD8^+$ cells.

4. A method of claim 1, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

5. A method of claim 4, wherein the virus is CMV.

6. A method of claim 1, wherein the monocyte-derived macrophages are human.

7. A method for screening for inhibitors of virus production using virally permissive monocyte-derived macrophages, the method comprising the steps of:
   (a) culturing monocytes under conditions where the monocytes are in fluid communication with viable, allogeneically stimulated peripheral blood mononuclear cells (PBMC) to activate the monocytes to differentiate into virally permissive monocyte-derived macrophages;
   (b) permitting viral replication in the monocyte-derived macrophages, where the virus is either latent in the monocytes or exogenously added to the culture;
   (c) contacting the monocyte-derived macrophages of step (b) with substances suspected of having the ability to inhibit viral production; and
   (d) detecting the level of virus production in the monocytes-derived macrophages.

8. A method of claim 7, wherein the monocyte-derived macrophages have a majority population of cell bearing CD83 and CD14.

9. A method of claim 7, wherein the monocyte derived-macrophages have a majority population of cells bearing CD83, CD68, CD1a, CD64, and CD14.

10. A method of claim 7, wherein the allogeneically stimulated cells include $CD4^+$ and $CD8^+$ cells.

11. A method of claim 7, wherein the virus is latent.

12. A method of claim 7, wherein the monocyte-derived macrophages are human.

13. A method of claim 7, wherein the substances are inhibitors of viral proteases.

14. A method of claim 7, wherein the substances are antisense molecules that bind to nucleic acid generated by the virus.

15. A method of claim 7, wherein the substances are antisense molecules that are complementary to mRNA encoded by a viral genome.

16. A method of claim 15, wherein the substances are ribozymes complementary to MRNA encoded by a viral genome.

17. A method of claim 7, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

18. A method of claim 17, wherein the virus is CMV.

19. A method of claim 17, wherein the substances inhibit a viral protein selected from the group consisting of CMV DNA polymerase, UL80, and UL89.

20. A stable culture of virally permissive monocyte-derived macrophages, wherein the monocyte-derived macrophages are derived from monocytes exposed to allogeneically stimulated peripheral blood mononuclear cells (PBMC) for a time sufficient to and a concentration sufficient to: (i) stimulate active differentiation of the monocytes into monocyte-derived macrophages, and (ii) stimulate viral production in the monocyte-derived macrophages; and, wherein the virally permissive monocyte-derived macrophages produce at least 10,000 fold greater virus than non-allogeneically stimulated monocytes, and wherein the monoczte derived-macrophages have a majority population of cells bearing CD83 and CD14.

21. A culture of claim 20, wherein the monocyte derived-macrophages have a majority population of cells bearing CD83, CD68, CD1a, CD64, and CD14.

22. A culture of claim 20, wherein the monocyte-derived macrophages produce a virus selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

23. A culture of claim 22, wherein the virus is CMV.

24. A stable culture of virally permissive monocyte-derived macrophages having a population defined as at least 85% bearing CD83 and CD14.

25. A culture of claim 24, wherein the monocyte derived-macrophages have a population of at least 85% of the cells bearing CD83, CD68, CD1a, CD64, and CD14.

26. A culture of claim 24, wherein the virus is latent.

27. A culture of claim 24, wherein the monocyte-derived macrophages produce a virus selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HH8).

28. A culture of claim 27, wherein the virus is CMV.

29. A culture of claim 24, wherein the monocyte-derived macrophages are human.

30. A method of culturing virally permissive monocyte-derived macrophages, the method comprising the step of culturing monocytes under conditions where the monocytes are in fluid communication with viable, allogeneically stimulated peripheral blood mononuclear cells (PBMC) to activate the monocytes to differentiate into monocyte-derived macrophages, wherein the monocyte derived-macrophages have a majority population of cells bearing CD83 and CD14.

31. A method of claim 30, wherein the monocyte derived-macrophages have a majority population of cells bearing CD83, CD68, CD1a, CD64, and CD14.

32. A method of claim 30, wherein the allogeneically stimulated cells include CD4$^+$ and CD8$^+$ cells.

33. A method of claim 30, wherein the monocyte-derived macrophages are human.

34. A stable culture of virally permissive monocyte-derived macrophages having the following characteristics:
   (i) comprising dendritic cell markers CD68, CD83, and CD1a;
   (ii) comprising macrophage cell markers CD64 and CD14; and
   (iii) derived from CD14$^+$ monocytes.

35. A method of replicating viruses in virally permissive monocyte-derived macrophages, the method comprising the steps of:
   (a) culturing CD14$^+$ monocytes under conditions where the monocytes are exposed to conditioned media comprising IFNγ in an amount sufficient to activate the monocytes to differentiate into virally permissive monocyte-derived macrophages; and
   (b) permitting viral replication in the monocyte-derived macrophages, where the virus is either latent in the monocytes or exogenously added to the culture, and wherein the monocyte derived-macrophages have a majority population of cells bearing CD83 and CD14.

36. A method of claim 35, wherein the monocyte derived-macrophages have a majority population of cells bearing CD83, CD68, CD1a, CD64, and CD14.

37. A method of claim 35, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

38. A method of claim 37, wherein the virus is CMV.

39. A method of claim 35, wherein the monocyte-derived macrophages are human.

40. A method for screening for inhibitors of virus production using virally permissive monocyte-derived macrophages, the method comprising the steps of:
   (a) culturing CD 14$^+$ monocytes under conditions where the monocytes exposed to conditioned media comprising IFNγ in an amount sufficient to activate the monocytes to differentiate into virally permissive monocyte-derived macrophages;
   (b) permitting viral replication in the monocyte-derived macrophages, where the virus is either latent in the monocytes or exogenously added to the culture;
   (c) contacting the monocyte-derived macrophages of step (b) with substances suspected of having the ability to inhibit viral production; and
   (d) detecting the level of virus production in the monocytes-derived macrophages.

41. A method of claim 40, wherein the monocyte-derived macrophages have a majority population of cell bearing CD83 and CD14.

42. A method of claim 40, wherein the monocyte derived-macrophages have a majority population of cells bearing CD83, CD68, CD1a, CD64, and CD14.

43. A method of claim 40, wherein the virus is latent.

44. A method of claim 40, wherein the monocyte-derived macrophages are human.

45. A method of claim 40, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

46. A method of claim 45, wherein the virus is CMV.

47. A stable culture of virally permissive monocyte-derived macrophages, wherein the monocyte-derived macrophages are derived from CD14$^+$ monocytes exposed to conditioned media comprising IFNγ in an amount sufficient to and for a time sufficient to: (i) stimulate active differentiation of the CD14$^+$ monocytes into monocyte-derived macrophages, and (ii) stimulate viral production in the monocyte-derived macrophages; and, wherein the virally permissive monocyte-derived macrophages produce at least 10,000 fold greater virus than non-allogeneically stimulated monocytes.

48. A culture of claim 47, wherein the majority of the monocyte-derived macrophages bear CD83 and CD14.

49. A culture of claim 47, wherein the majority of the monocyte-derived macrophages bear CD83, CD68, CD1a, CD64, and CD14.

50. A culture of claim 47, wherein the monocyte-derived macrophages produce a virus selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

51. A culture of claim 50, wherein the virus is CMV.

52. A stable culture of virally permissive monocyte-derived macrophages having a population defined as at least 85% bearing CD83 and CD14.

53. A culture of claim 52, wherein the population has at least 85% of the cells bearing CD83, CD68, CD1a, CD64, and CD14.

54. A culture of claim 52, wherein the virus is latent.

55. A culture of claim 52, wherein the monocyte-derived macrophages produce a virus selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

56. A culture of claim 55, wherein the virus is CMV.

57. A culture of claim 52, wherein the monocyte-derived macrophages are human.

58. A method of culturing virally permissive monocyte-derived macrophages, the method comprising the step of culturing CD14$^+$ monocytes under conditions where the monocytes are exposed to conditioned media comprising IFNγ in an amount sufficient to activate the monocytes to differentiate into virally permissive monocyte-derived macrophages, and wherein the monocyte derived-macrophages have a majority population of cells bearing CD83 and CD14.

59. A method of claim 58, wherein the monocyte derived-macrophages have a majority population of cells bearing CD83, CD68, CD1a, CD64, and CD14.

60. A method of claim 58, wherein the monocyte-derived macrophages are human.

61. The method of claim 1, wherein the virus is hepatitis C virus (HCV).

62. The method of claim 7, wherein the virus is hepatitis C virus (HCV).

63. The method of claim 20, wherein the virus is hepatitis C virus (HCV).

64. The method of claim 35, wherein the virus is hepatitis C virus (HCV).

65. The method of claim 40, wherein the virus is hepatitis C virus (HCV).

66. The method of claim 47, wherein the virus is hepatitis C virus (HCV).

67. Virus made using the method of claim 1.

68. The virus of claim 67, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

69. Virus of claim 67, wherein, the virus is hepatitis C virus (HCV).

70. Infective virus made using the method of claim 38.

71. The virus of claim 70, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

72. The virus of claim 70, wherein the virus is hepatitis C virus (HCV).

73. A method of infecting cells with virus, the method comprising the steps of:
(a) culturing monocytes under conditions where the monocytes are in fluid communication with viable, allogeneically stimulated peripheral blood mononuclear cells (PBMC) to activate the monocytes to differentiate into virally permissive monocyte-derived macrophages;
(b) permitting virus replication in the monocyte-derived macrophages, where the virus is either latent in the monocytes or exogenously added to the culture;
(c) collecting virus from the culture; and
(d) contacting a second culture of cells with the virus, thereby infecting the cells with the virus.

74. The method of claim 73, wherein the second culture of cells comprises fibroblasts.

75. The method of claim 73, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

76. The method of claim 73, wherein the virus is hepatitis C virus (HCV).

77. A method of infecting cells with virus, the method comprising the steps of:
(a) culturing CD14$^+$ monocytes under conditions where the monocytes are exposed to conditioned media comprising IFNγ in an amount sufficient to activate the monocytes to differentiate into virally permissive monocyte-derived macrophages;
(b) permitting viral replication in the monocyte-derived macrophages, where the virus is either latent in the monocytes or exogenously added to the culture.
(c) collecting virus from the culture; and
(d) contacting a second culture of cells with the virus, thereby infecting the cells with the virus.

78. The method of claim 77, wherein the second culture of cells comprises fibroblasts.

79. The method of claim 77, wherein the virus is selected from the group consisting of cytomegalovirus (CMV), hepatitis C virus (HCV), human immunodeficiency virus (HIV), human herpes virus 6 (HHV6), human herpes virus 7 (HHV7), and human herpes virus 8 (HHV8).

80. The method of claim 77, wherein the virus is hepatitis C virus (HCV).

\* \* \* \* \*